United States Patent [19]

Steiner et al.

[11] 4,134,908

[45] Jan. 16, 1979

[54] METHANATION PROCESS

[75] Inventors: Peter Steiner, Edison; Ernest L. Daman, Westfield, both of N.J.

[73] Assignee: Foster Wheeler Energy Corporation, Livingston, N.J.

[21] Appl. No.: 791,755

[22] Filed: Apr. 28, 1977

[51] Int. Cl.² .............................................. C07C 1/04
[52] U.S. Cl. .......................... 260/449.6 M; 252/477 R; 422/197; 422/229
[58] Field of Search .................... 260/449 M, 449.6 M, 260/449.6 R, 449 R; 23/288 M, 288 L, 288 K; 48/180

[56] References Cited

U.S. PATENT DOCUMENTS

| | | | |
|---|---|---|---|
| 1,815,177 | 7/1931 | Balachowsky et al. | 48/180 R |
| 1,815,178 | 7/1931 | Balachowsky et al. | 48/180 R |
| 2,526,657 | 10/1950 | Guyer | 23/288 M |
| 2,662,911 | 12/1953 | Dorschner et al. | 260/449 R |
| 3,156,544 | 11/1964 | Eck et al. | 48/102 |
| 3,359,215 | 12/1967 | Reitmeier | 252/459 |
| 3,625,665 | 4/1969 | Thompson | 260/449 M |
| 3,922,148 | 11/1975 | Child | 260/449 M |
| 3,947,939 | 4/1976 | Steiner | 138/42 |
| 3,970,435 | 7/1976 | Schultz et al. | 260/449 M |
| 4,010,008 | 3/1977 | Jo | 260/449 M |

FOREIGN PATENT DOCUMENTS 2332686  1/1974  Fed. Rep. of Germany ........... 252/373

*Primary Examiner*—Howard T. Mars
*Attorney, Agent, or Firm*—Marvin A. Naigur; John J. Herguth, Jr.; John E. Wilson

[57] ABSTRACT

A process and apparatus for producing methane by reacting carbon monoxide with hydrogen, the improvement comprising feeding a gas containing hydrogen and carbon monoxide into at least one tubular reactor containing a helical, nickel-containing catalyst (turbulator) are disclosed. The catalyst defines a spiral-shaped path for the gas. The exterior of the reaction tube is cooled to remove the heat of reaction. Preferably, additional heat of reaction is removed by passing a cooling medium through the center of the turbulator catalyst.

4 Claims, 10 Drawing Figures

METHANATION PROCESS

FIELD OF THE INVENTION

The present invention is an improved process and apparatus for the production of methane from gases rich in carbon monoxide and hydrogen.

BACKGROUND OF THE INVENTION

"Methanation" is the name given to a catalytic reaction which yields methane gas from carbon monoxide and hydrogen according to the equation:

$$CO + 3H_2 = CH_4 + H_2O + \text{heat}. \quad (1)$$

The limited availability of methane from natural sources coupled with the enormous utility of methane as a clean, sulfur-free fuel combine to create a great need for "synthetic natural gas." Methane by methanation now holds great economic significance because the reactants can be obtained by the reaction of the more readily available coal with steam according to the basic equations:

$$2C + 2H_2O = 2CO + 2H_2 \quad (2)$$

$$CO + H_2O = CO_2 + H_2 \quad (3)$$

$$2C + 3H_2O = CO_2 + CO + 3H_2 \quad (4)$$

Since reaction (2) requires heat input, oxygen/air is added to the reactants and the products therefore contain carbon dioxide and nitrogen.

Reaction (1) is highly exothermic and is reversible so that high temperatures tend to reduce the yield of methane. Accordingly, efficient heat removal poses a problem in all methanation processes. Conventional prior art methanation processes are conducted by passing the gaseous reactants through a packed bed of a catalyst which is typically nickel or nickel alloyed with platinum. Such a process is disclosed for example, in U.S. Pat. No. 3,930,812 issued to Harris et al. Harris et al control temperature by injecting liquid water into the reaction zone which removes heat by vaporization. However, the packed bed processes such as that of Harris et al are characterized by a large pressure drop across the reactor.

Dorschner et al, U.S. Pat. No. 2,662,911, approaches the heat removal problem by conducting the reaction in a plurality of catalyst packed tubes, vertically arranged in a water-containing drum. Dorschner, U.S. Pat. No. 2,740,803, discloses methanation in a fluidized bed provided with double-walled, bayonet type heat exchangers through which water is passed (FIG. 4). This latter Dorschner patent also discloses an embodiment (FIG. 1) wherein the catalyst is passed into "contact tubes vertically arranged in a water-containing drum and having diameters which progressively decrease from the top to the bottom." These methods, like the more conventional packed bed methods, are also characterized by high pressure drops across the reactor.

All of the foregoing prior art methanation processes are characterized by the use of a granular or particulate catalyst which tends to generate coke and plug up over prolonged periods of usage.

SUMMARY OF THE INVENTION

The present invention provides a method for producing methane gases containing hydrogen and carbon monoxide in admixture by passing the gaseous reactants through at least one catalytic turbulator which defines a helical or spirial flow path through the reactor. The turbulator may be fabricated of nickel, platinum, alloys thereof, or any of these metals plated or deposited on a dissimilar metal prefabricated into the shape of the turbulator.

In addition to providing for efficient cooling of the reaction zone and heat recovery, the present invention enables operation of the methanation process with a very low pressure drop across the reactor. The present invention provides a catalytic reactor wherein the channel in which the gaseous reactants flow is 90% by volume open space as contrasted with the conventional packed bed reactors which typically have about 30% by volume open space. This difference explains the reduced pressure drop across the reactors of the present invention as contrasted with the prior art reactors.

The prior art limitation on minimum tube diameter, which is dictated by the granular nature of the prior art catalyst is eliminated by the present invention, thereby making it feasible to design reactors for operation at higher pressures than heretofore has been possible. Operation at higher pressures enables a favorable shift in the equilibrium of reversible reaction (1) thus enabling higher yields.

In the preferred embodiment of the present invention, an apparatus is provided wherein the turbulator catalytic strip or ribbon surrounds a centrally disposed tube, with the turbulator in turn covered by an outer sheath or tube. In the preferred embodiments the capability for passing a cooling medium through the central tube, in addition to around the exterior of the outer tube or sheath, optimizes temperature control of the methanation reaction. In these preferred embodiments the gaseous reactants/products follow a spiral path through the annular space defined between the inner tube and the outer sheath.

Accordingly, it is an object of the present invention to provide for the production of methane from gaseous mixtures containing hydrogen and carbon monoxide with improved heat and mass transfer.

It is a further object of the present invention to provide for reduced pressure drop through the reactor.

Yet another object of the present invention is to provide a tubular reactor for methanation without limitation on the minimum tube diameter.

It is still another object of the present invention to provide a method and apparatus for methanation which require less catalyst material.

Yet another object of the present invention is to provide a reactor for methanation having a catalyst capable of prolonged periods of usage without deactivation, coking or plugging.

These and other objects and further scope of applicability of the present invention will become apparent from a reading of the detailed description to follow, taken in conjunction with the accompanying drawing.

DESCRIPTION OF THE PREFERRED EMBODIMENTS

The feed gases which may be subjected to methanation in accordance with the present invention include all the various feed gases used in the conventional methanation processes. For example, suitable feed gases include (but are not limited to) those generated from coal in accordance with equation 4 as previously described. The feed gases are characterized by the presence of economically significant amounts of hydrogen and carbon monoxide. The volume ratio of hydrogen to carbon monoxide will typically range from 1:1 to 3:1 and preferably from 1.5:1 to 2.3:1.

The operating parameters employed in connection with the present invention are generally conventional. However, the operating pressure may be somewhat greater than conventional. Typically, the operating temperature will range from 600 to 1300° F. and the operating pressure from 200 to 500 psig or higher. The space velocity through the reactor will vary widely in accordance with the operating pressure. Typically, the gas space velocity will range from 1800 to as high as 8000 v/v/hr. With the present invention, methane is obtained in high yields, e.g. product gases wherein methane constitutes 30 to 40% by volume.

Optionally, the feed gases may be preheated. Suitable preheat temperatures will vary with pressure and other conditions and may range from 600 to 1200° F.

Figure 1:
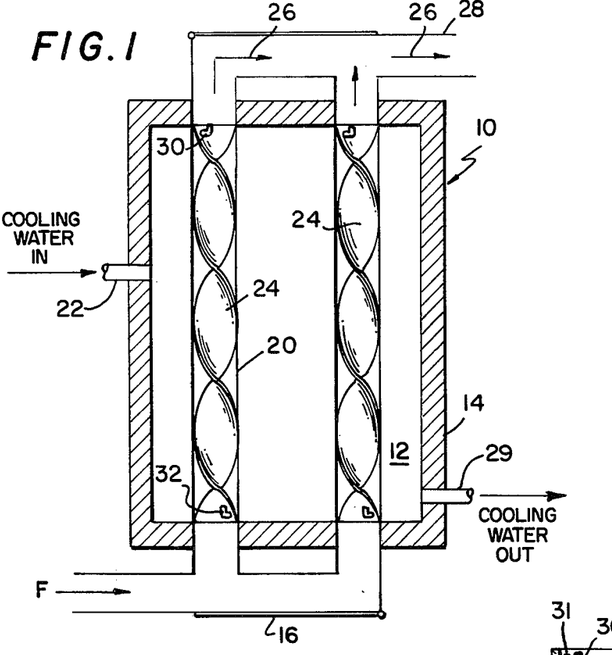
FIG. 1 is a schematic front elevational view of a reactor vessel containing a plurality of methanation tubes in accordance with the present invention.
Figures 3, 4:
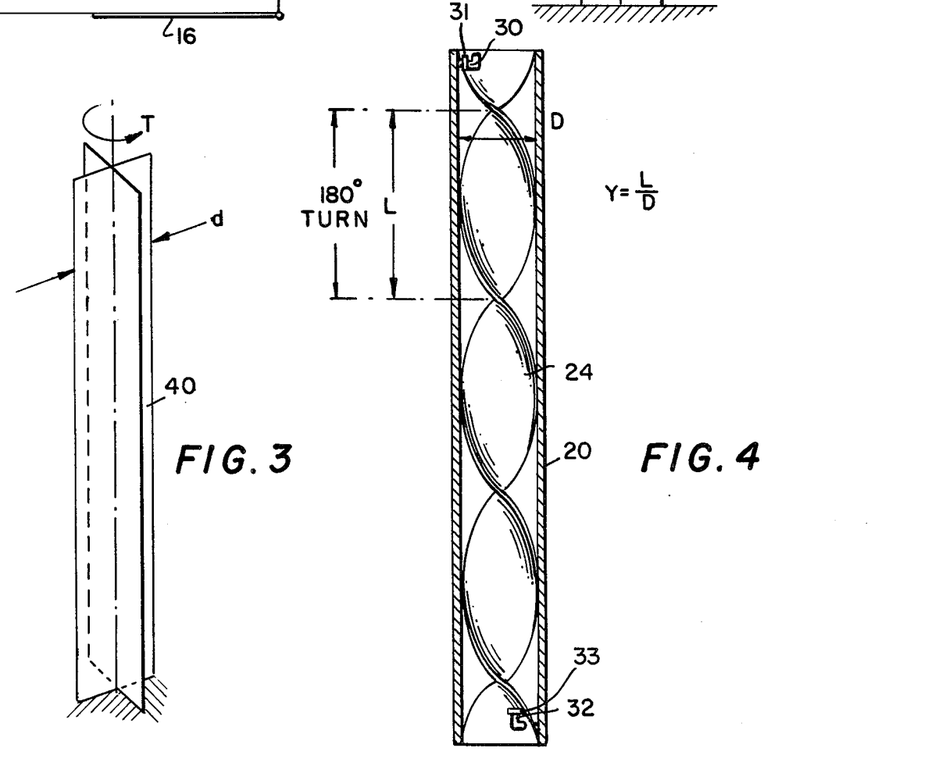
FIG. 3 is a perspective view, similar to FIG. 2, of a pair of perpendicular intersecting metal strips.
FIG. 4 is a schematic elevational enlarged view of one of the reactor tubes of the reactor shown in FIG. 1, shown in cross-section.

Referring now specifically to the drawings, there is shown schematically in FIG. 1 a reactor vessel 10 formed with an internal chamber 12 defined by a rectangular wall 14. A plurality of tubes 20 are disposed in the internal chamber 12 and an inlet conduit 16 is connected to the tubes 20 for conveying the feed stock F. Means for introducing a cooling fluid into the space surrounding tubes 20 is shown at 22 and an exit at 29. An activated nickel containing catalyst in the form of a turbulator 24 is housed within each of the tubes 20. In this manner, the feed gas passes into the tubes 20 and the carbon monoxide and hydrogen are brought into indirect heat exchange with the cooling medium, and react in the presence of the catalytically active turbulator 24 to produce a methane-rich synthesis gas which exits through the outlet conduit 28 as indicated by the directional arrows 26. The turbulators are maintained in a fixed position in the tubes 20 by means of an upper snap hook 30 and a lower snap hook 32 which are located at the respective upper and lower ends of the tubes 20. As best shown in FIG. 4, the turbulators 24 are formed with openings 31 and 33 for receiving snap hooks 30 and 32.

Figure 5:
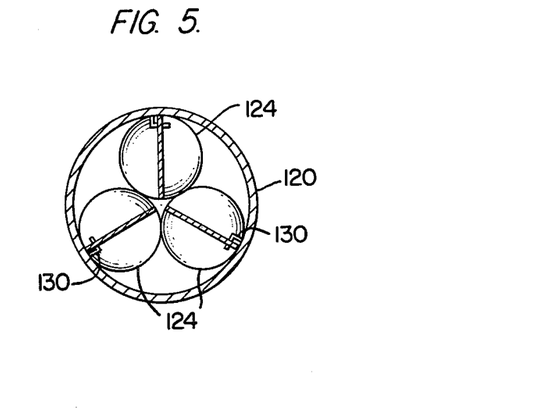
FIG. 5 is an enlarged sectional view of an methanation tube similar to FIG. 4 but with three twisted strips housed within the tube.

In FIG. 5 there is illustrated a further embodiment of the invention in which corresponding parts have been designated by the same reference numerals as part of a "100" series. In this embodiment, a methanation tube 120 contains a nickel catalyst in the form of a plurality of activated turbulators 124. In this manner, the feed stock may be passed through the tube or tubes 120 and the carbon monoxide and hydrogen will react catalytically with the turbulators 124 to produce a methane rich gaseous product. The three turbulators 124 shown in FIG. 5 are maintained in a fixed position in the tubes 120 by means of upper snap hooks 130 and lower snap hooks (not shown) which are located at the respective ends of the tube 120.

Figure 6:
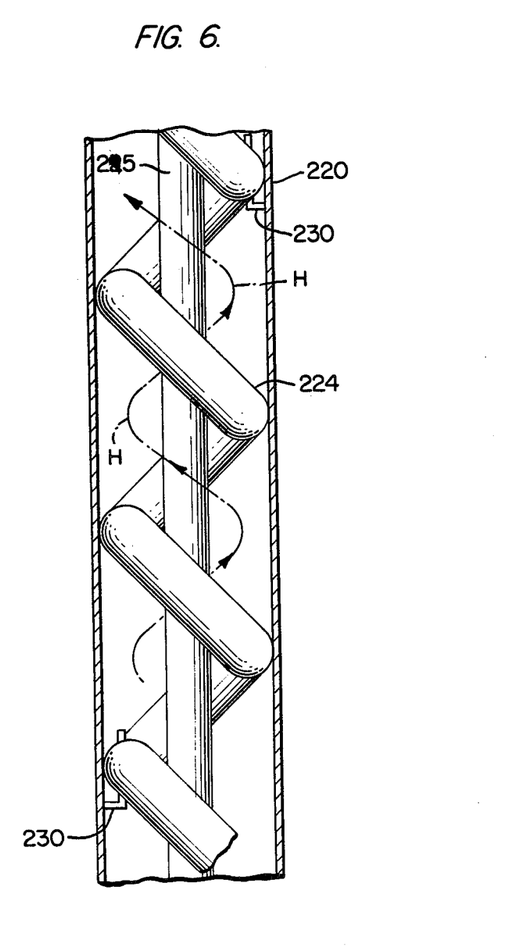
FIG. 6 is a sectional view of another embodiment of a methanation reactor tube showing a coiled turbulator positioned around a central rod within the tube.

In FIG. 6 there is illustrated yet another embodiment of the present invention in which corresponding parts have been designated by the same reference numerals as part of a "200" series. In this form of the invention there is shown a methanation tube 220 for supporting the nickel containing catalyst in the form of an activated turbulator 224 which is coiled or twisted around a rod 225. The turbulator 124 is welded to rod 225 so that a helical path is formed between the turbulator 224 in the inner walls of the tube 220 as denoted by the helical directional arrow H. In this manner, the feedstock passes into the tubes 220 and the carbon monoxide and hydrogen react on the exterior surface of the twisted tubular turbulator 224 to produce a methane-rich gaseous product. If desired, a cooling medium can be passed through the center of the tubular turbulator 224 to increase cooling capacity. The turbulator 224 and rod 225 shown in FIG. 6 are maintained in a fixed position in the tubes 220 by means of upper snap hooks 230 and lower snap hooks 232 which are located at the respective ends of the tube 220.

Figure 8:
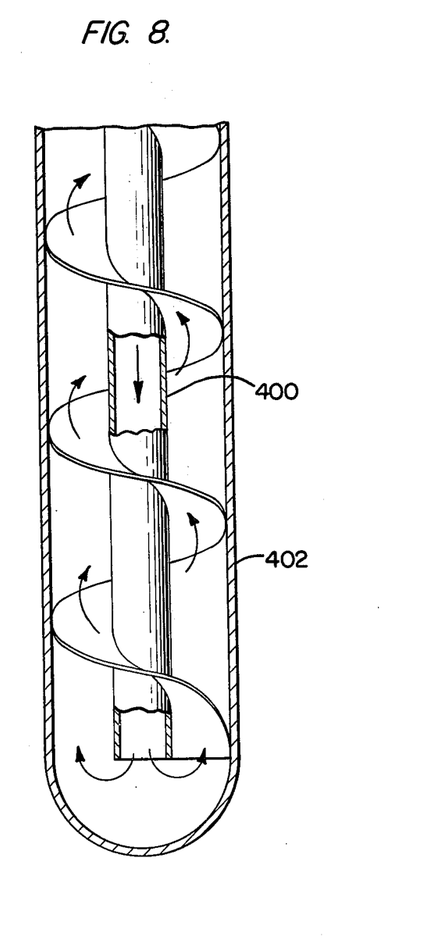
FIG. 8 is a schematic elevational view, in crosssection, of a preferred embodiment of the present invention wherein the catalytic strip is twisted on edge around a central cooling tube.
Figure 9:
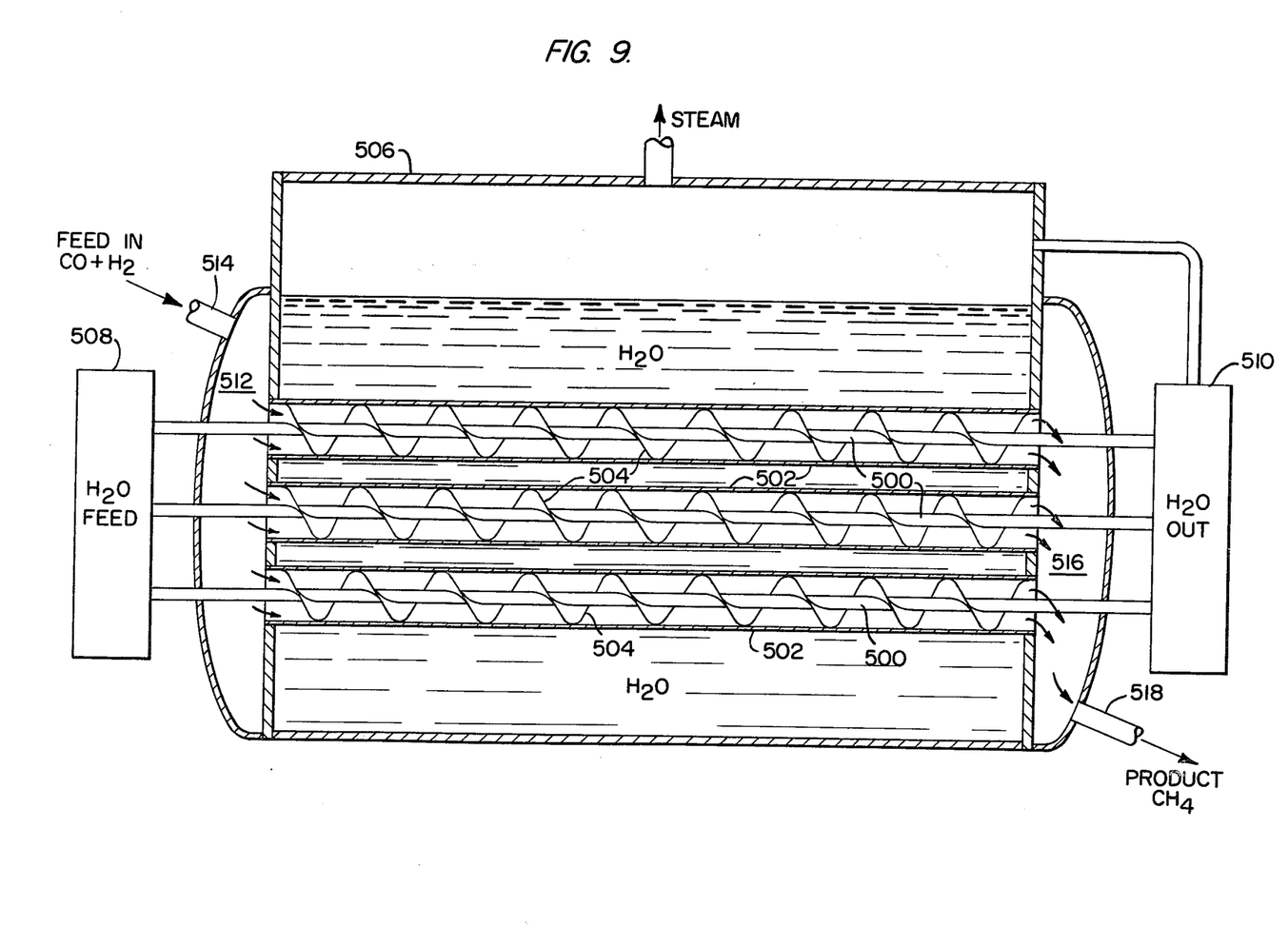
FIG. 9 is a schematic elevational view, partially in cross-section, of a reactor vessel containing methanation tubes of another preferred embodiment wherein the catalytic strip or ribbon is twisted around a central cooling tube.

Because of the highly exothermic nature of the methanation reaction, in the preferred embodiments the turbulator is wrapped around a central cooling passage so that a cooling medium may be passed both through the center of the turbulator reactor and around the exterior thereof, as in the embodiments illustrated in FIGS. 8 and 9. In these embodiments, the catalyst is helically disposed in an annular passageway. In the center of the annulus is a tube for receiving a first cooling medium, shown as 400 in FIG. 8, and designated as 500 in FIG. 9. A second cooling medium is circulated around in outside of the exterior or sheath tube 402 in FIG. 8 and 502 in FIG. 9. In the embodiment of FIG. 9 the first and second cooling mediums may be the same. In FIG. 8 the first cooling medium is the feed gas itself which, after reaching the bottom of the tube, reverses and flows over the turbulator inside the sheath tube 402. The advantage of these preferred embodiments is that the ratio of catalyst surface to heat conducting surface is reduced so that the cooling capacity of the methanator is optimized. As previously indicated the embodiment of FIG. 6 can also be used in the preferred technique by passing a cooling fluid through the center of the turbulator.

In the embodiment of FIG. 9 a plurality of methanation tubes are arranged in parallel through a steam drum 506. Each methanation tube is formed of an outer tube or sheath 502 containing a catalytic turbulator in the form of a strip of nickel-containing metal 504 helically wrapped on edge around a central cooling tube 500. At their inlet ends, the cooling tubes 500 are connected to a water header 508 which supplies the internal or first cooling medium to the methanation tubes. The cooling water exits tubes 500 into a second header 510 from which the super-heated water or mixed aqueous phase is injected into the steam drum. The water headers, of course, are optional and may be dispensed with entirely. The feed gas enters gas header 512 through an inlet 514 and then passes through the annular interior space of the methanation tubes defined by tubular members 500 and 502. In passing through the annular space within the methanation tubes the feed gas follows a spiral path along the surface of the catalytic strip or ribbon 504. Finally, the gas exits the methanation tubes as a product containing methane into gas header 516 and exits through outlet 518 as a useful product containing methane.

Figure 2:
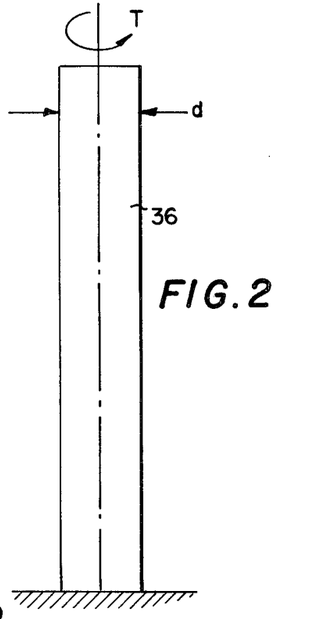
FIG. 2 is an elevational view of a flat metal strip supported at one end, with the arrow at the opposite end indicating the twisting cold working process.

The turbulators of the present invention may be fabricated by conventional cold-working techniques. For example, turbulators such as are shown in FIGS. 1 and 4 may be fabricated merely be securing a flat strip or ribbon, such as shown as element 36 in FIG. 2, at its ends and twisting the strip through a series of 180° rotations as indicated by the circular directional arrow T. Turbulators similar to those of FIGS. 1 and 4 may be formed by similar twisting of the perpendicular element 40 shown in FIG. 3. Such turbulators are characterized by a generally sinusoidal shape. As indicated in FIG. 4, the degree of twist is designated by a Y factor which is equal to the length L of a single twist T divided by the diameter D of tube 20 (or d of FIGS. 2 and 3). A typical range for the Y factor of the catalyst used in the present invention is 2.0 to 3.0. In terms of catalytic efficiency, a small Y factor is preferred. In other words, the smaller the Y factor, the higher the degree of twist. The lower limit of the Y factor is determined by the mechanical properties of the catalytic metal, i.e. the degree of twisting which it will undergo before breakage. Accordingly, where the nature of the catalytic metal permits, turbulators having Y factors less than 2.0 may be fabricated.

The dimensions or shapes of the catalytic strips or ribbons used in the present invention are not critical and will vary widely with the reactor design, the diameter of the tubular reactor, etc. For the purpose of the present invention a ribbon can be defined as any elongated member of a rectangular cross-section.

In the present invention the turbulator-type catalyst is fabricated from nickel metal or a nickel-containing alloy in which nickel is a mjaor constituent. Alternately, the turbulator itself may be of a dissimilar metal, with the nickel catalyst plated or coated by deposition on its surface. In the case of fabrication of the turbulator from nickel or nickel-alloy strip, the cold-working serves to activate the catalyst by producing stresses as disclosed in more detail in copending application U.S. Ser. No. 572,797, filed Apr. 29, 1975 and now abandoned, the teachings of which are herein incorporated by reference.

The turbulators which serve as the catalyst in the present invention provide a helically shaped passageway for the gaseous reactants along and through the length of the reactor. In performing such a function, the turbulators can assume any one of a variety of configurations. In the embodiments of FIGS. 1 and 4 the catalyst is in the form of a single twisted flap strip or ribbon which substantially fills the turbulator reactor. Turbulators of like configuration are disclosed in U.S. Pat. No. 1,809,114. In the embodiments of FIGS. 1 and 4 a plurality of such strips placed end to end, would provide an equivalent structure. In the embodiment of FIG. 5 a plurality of flat twisted elongated strips are arranged in parallel along the length of the reactor.

Figure 7:
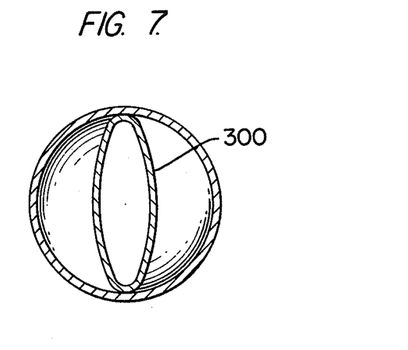
FIG. 7 is a top cross-sectional view of a methanation reaction tube wherein the catalytic turbulator is in the form of a twisted piece of tubing.

In still other embodiments, the turbulator may be formed from tubing rather than from flat strips, e.g. as in the embodiments of FIGS. 6 and 7.

In the embodiment of FIG. 7 the turbulator is an elongated section of twisted flattened tubing, as may be formed by twisting the tube 300 while under tension.

A method for forming turbulators of suitable configuration is disclosed in more detail in U.S. Pat. Nos. 3,947,939 and 3,969,037, both issued to Peter Steiner and entitled "METHOD FOR THE MANUFACTURE OF TURBULATORS", the teachings of which are incorporated herein by reference.

EXAMPLES

Figure 10:
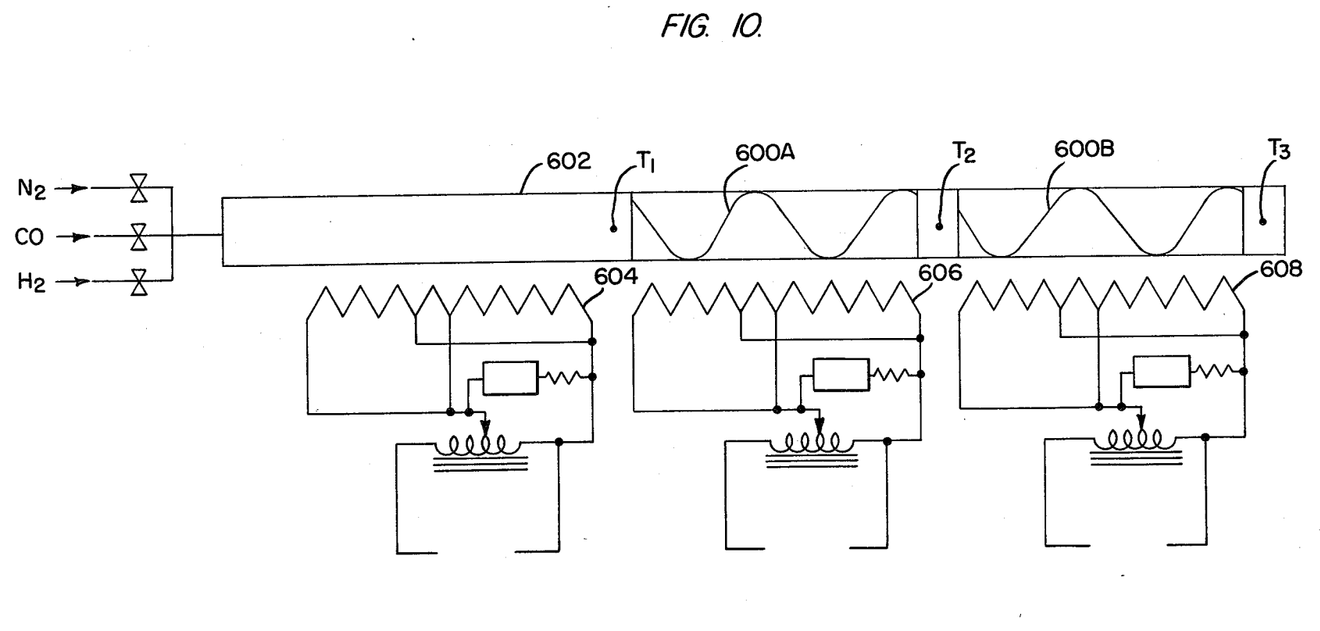
FIG. 10 is a schematic illustration of the bench methanator used in the examples of the specification.

A "bench methanator", as illustrated in FIG. 10, was used in a series of tests conducted in accordance with the present invention. The catalyst 600 in the test methanator consisted of two pieces of nickel strip of ⅛ inch by 1.1 inch nickel, each measuring 18 inches in length. The catalyst was fabricated by holding each strip in a lathe and twisting it so that 180 degrees of twist was equal to 1.6 pipe diameters. The lathe maintained the strip at constant length during forming. The edges of the twisted strip pieces were ground slightly to fit them into a 1 inch schedule 40 Incalloy 800 reactor tube 602. A 1 inch space was left between the two catalyst sections A and B to permit access for a process stream thermocouple T2. The reactor measured 80 inches in length with a preheating section of 33½ inches. Three electric heaters 604, 606 and 608 were used to heat the reactor tube.

The turbulator length was 36 inches and its Y factor was 1.612 pipe diameters/180 degrees.

In the tests summarized in tables 1 and 2 the catalyst was activated by passing hot nitrogen through the reactor, i.e. runs (3) described in table 1. The results for test runs 12, 13 and 14 are summarized in table 2.

While these tests illustrate commercial feasibility of methanation with a turbulator catalyst, the methanation unit used had obvious shortcomings, specifically in the lack of any means for continuously removing the heat of reaction. Due to this shortcoming in the apparatus local overheating problems were experienced. Accordingly, the present invention contemplates the use of a cooling fluid to be circulated around the exterior of the methanation tubes. Moreover, as previously noted, in the preferred embodiments a second cooling medium is passed through a central tube which is surrounded by the turbulator catalyst.

TABLE I
Run Data

| Run No. | 9 | 9 | 10 | 10 | 11 | 11 | 11 | (3) | 12 | 13 | 13 | 13 | 13 | (3) | 14 |
|---|---|---|---|---|---|---|---|---|---|---|---|---|---|---|---|
| Sample No. | 11 | 12 | 13 | 14 | 15 | 16 | 17 | | 18 | 19 | 20 | 21 | 22 | | 23 |
| Realtor: | | | | | | | | | | | | | | | |
| Inlet Gas Temp., °F | 887 | 918 | 913 | 912 | 838 | 850 | 854 | 1365 | 800 | 742 | 600 | 645 | 784 | 1537 | 800 |
| Center Gas Temp., °F | (2) | (2) | (2) | (2) | (2) | (2) | (2) | 1364 | 1077 | 950 | 855 | 682 | 782 | 1676 | 1007 |
| Outlet Gas Temp., °F | 950 | 900 | 916 | 912 | 900 | 892 | 877 | 1558 | 890 | 947 | 1005 | 1020 | 1011 | 1589 | 785 |
| Outlet Pressure, psig | 293 | 297 | 297 | 297 | 302 | 302 | 303 | 110 | 990 | 990 | 980 | 970 | 970 | 100 | 1010 |
| Feed: | | | | | | | | | | | | | | | |
| Hydrogen, SCFH | 36.8 | 36.8 | 36.8 | 36.8 | 36.8 | 36.8 | 36.8 | | 40.6 | 39.2 | 41.0 | 41.0 | 41.0 | | 40.3 |
| Carbon Monoxide, SCFH | 8.0 | 8.0 | 10.0 | 10.0 | 12.0 | 12.0 | 12.0 | | 7.0 | 12.9 | 13.4 | 13.4 | 13.4 | | 11.7 |
| Water, milliliters per hour | 345 | 303 | 302 | 302 | 120 | 126 | 123 | 240 | 84 | 90 | 97 | 96 | 96 | 310 | 72 |
| Vol. Ratio H₂/CO | 4.6 | 4.6 | 3.7 | 3.7 | 3.1 | 3.1 | 3.1 | | 5.8 | 3.0 | 3.1 | 3.1 | 3.1 | | 3.4 |
| Product (Dry): | | | | | | | | | | | | | | | |
| Volume, SCFH | 25.9 | 26.0 | 24.1 | 24.6 | 27.4 | 28.4 | 29.3 | | 28.7 | 24.3 | 24.5 | 26.9 | 26.2 | | 20.8 |
| Analysis, Vol.%: | | | | | | | | | | | | | | | |
| N₂ | 1.8 | 4.8 | 2.6 | 3.3 | 1.7 | | 1.3 | | 2.6 | 0.5 | 0.4 | 0.3 | 0.3 | | 0.5 |
| CO | 1.5 | 0.1 | 1.7 | 1.7 | 7.5 | | 8.1 | | 0.1 | 3.3 | 4.3 | 4.9 | 6.0 | | 0.4 |
| CH₄ | 21.4 | 17.7 | 33.8 | 29.9 | 28.3 | | 24.4 | | 24.8 | 47.3 | 42.8 | 37.8 | 37.9 | | 54.5 |
| CO₂ | 6.5 | 1.6 | 8.1 | 13.0 | 10.3 | | 10.4 | | 0.2 | 7.3 | 7.6 | 7.4 | 7.3 | | 3.5 |
| H₂ | 68.8 | 75.8 | 53.8 | 52.1 | 52.2 | | 55.8 | | 72.3 | 41.6 | 44.9 | 49.6 | 48.5 | | 41.1 |
| Conversion (to CH₄ & CO₂)% | 94.9 | 99.5 | 96.1 | 96.2 | 83.7 | | 81.1 | | 99.6 | 94.3 | 92.1 | 90.2 | 88.3 | | 99.3 |
| Selective Conversion, (to CH₄) | 0.73 | 0.91 | 0.78 | 0.67 | 0.57 | 0.57 | | | 0.82 | 0.78 | 0.76 | 0.74 | | | |
| Dry Vol. Ratio, Prod. to Feed | 0.58 | 0.58 | 0.52 | 0.53 | 0.73 | 0.60 | | 0.99 | 0.47 | 0.45 | 0.50 | 0.48 | | 0.93 | |
| Vol, Space-Time Yield (4) | 307 | 255 | 452 | 408 | 430 | 10.1 | 397 | 0.60 | 395 | 638 | 582 | 564 | 551 | 0.40 | 629 |
| Area Space-Time Yield (5) | 7.8 | 6.5 | 11.5 | 10.3 | 10.9 | 2710 | 10.0 | | 10.0 | 16.2 | 14.7 | 14.3 | 14.0 | | 15.9 |
| Space Velocity V/V/Hr. | 2490 | 2490 | 2600 | 2600 | 2710 | 0.50 | 2710 | | 2640 | 2890 | 3020 | 3020 | 3020 | | 2880 |
| Steam to Carbon Ratio | 2.05 | 1.80 | 1.43 | 1.43 | 0.48 | | 0.49 | | 0.57 | 0.33 | 0.34 | 0.34 | 0.34 | | 0.29 |
| Activation Purge Gas: | | | | | | | | | | | | | | | |
| Nitrogen, SCFH | | | | | | | | | | | | | | | |
| Breathing Air, SCFH | | | | | | | | 0.8 | | | | | | 0.8 | |
| Hydrogen, SCFH | | | | | | | | | | | | | | | |
| Activation Period, Hrs. | | | | | | | | 16 | | | | | | 16 | |

(1) Pipe diameters/180° of twist in nickel strip (⅛" thick).
(2) T.C. failed.
(3) Activation.
(4) Cu. Ft. of methane produced per hr./cu. ft. of catalyst.
(5) Cu. Ft. of methane produced per hr./sq. ft. of catalyst.

| Run No. | 14 | 14 | 14 | 14 | 14 | 14 | 14 | (4) | 15 | 15 | 15 | 15 | 15 | 16 | 17 |
|---|---|---|---|---|---|---|---|---|---|---|---|---|---|---|---|
| Sample No. | 24 | 25 | 26 | 27 | 28 | 29 | 30 | | 31 | 32 | 33 | 34 | 35 | 36 | 37 |
| Realtor: | | | | | | | | | | | | | | | |
| Inlet Gas Temp., °F | 700 | 670 | 713 | 708 | 708 | 760 | 786 | 880 | 910 | 896 | 1020 | 993 | 972 | 1039 | 1008 |
| Center Gas Temp., °F | 840 | 950 | 750 | 670 | 656 | 634 | 639 | 860 | 689 | 739 | 825 | 870 | 862 | 890 | 900 |
| Outlet Gas Temp., °F | 810 | 812 | 892 | 848 | 823 | 830 | 834 | 720 | 891 | 900 | 600 | 872 | 718 | 740 | 846 |
| Outlet Pressure, psig | 1000 | 1000 | 1000 | 1000 | 1020 | 1003 | 1000 | 1000 | 1000 | 1000 | 1000 | 1000 | 1000 | 1000 | 995 |
| Feed: | | | | | | | | | | | | | | | |
| Hydrogen, SCFH | 40.6 | 40.6 | 40.6 | 40.6 | 40.6 | 40.6 | 40.6 | | 40.6 | 40.6 | 40.6 | 40.6 | 40.6 | 40.6 | 40.6 |
| Carbon Monoxide, SCFH | 13.2 | 14.1 | 14.1 | 14.1 | 14.1 | 14.1 | 11.7 | 11.7 | 11.7 | 11.7 | 11.7 | 11.7 | 11.7 | 11.7 | |
| Water, milliliters per hour | 90 | 95 | 84 | 81 | 78 | 80 | 81 | 1120 | 100 | 108 | 96 | 108 | 110 | 72 | 80 |
| Vol. Ratio H₂/CO | 3.4 | 3.1 | 2.9 | 2.9 | 2.9 | 2.9 | 2.9 | | 3.5 | 3.5 | 3.5 | 3.5 | 3.5 | 3.5 | 3.5 |
| Product (Dry): | | | | | | | | | | | | | | | |
| Volume, SCFH | 18.3 | 21.6 | 23.4 | 24.0 | 23.6 | 24.0 | 22.5 | | 28.0 | 32.8 | 37.0 | 29.8 | 30.4 | 32.5 | 21.3 |
| Analysis, Vol. %: | | | | | | | | | | | | | | | |
| N₂ | 0.3 | 0.5 | 0.8 | 0.4 | 0.6 | 0.7 | 0.5 | | | | | | | 1.2 | 1.5 |
| CO | 1.0 | 1.3 | 3.2 | 3.0 | 2.9 | 3.0 | 2.9 | | | | | | | 4.2 | 0.9 |
| CH₄ | 49.4 | 54.0 | 51.0 | 51.2 | 55.1 | 52.1 | 52.1 | | | | | | | 26.3 | 46.1 |
| CO₂ | 4.3 | 6.7 | 9.2 | 9.3 | 8.6 | 8.5 | 9.0 | | | | | | | 6.8 | 4.4 |

TABLE I-continued

Run Data

| | | | | | | | | | |
|---|---|---|---|---|---|---|---|---|---|
| H₂ Conversion (to CH₄ & CO₂) % | 45.0 | 37.5 | 35.8 | 36.1 | 32.8 | 35.7 | 35.5 | 61.5 | 47.1 |
| Selective Conversion, (to CH₄) | 98.2 | 97.9 | 95.0 | 95.3 | 95.7 | 95.3 | 95.5 | 88.7 | 98.3 |
| Dry Vol. Ratio, Prod. to Feed | 0.90 | 0.87 | 0.80 | 0.81 | 0.83 | 0.82 | 0.81 | 0.71 | 0.90 |
| Vol., Space-Time Yield (5) | 0.35 | 0.40 | 0.43 | 0.44 | 0.43 | 0.44 | 0.41 | 0.62 | 0.41 |
| Area Space-Time Yield (6) | 501 | 647 | 662 | 682 | 721 | 694 | 650 | 474 | 545 |
| Space Velocity V/V/Hr. | 12.7 | 16.4 | 16.8 | 17.3 | 18.3 | 17.6 | 16.5 | 12.0 | 13.8 |
| | 2920 | 2980 | 3030 | 3030 | 3030 | 3030 | 3030 | 2900 | 2900 |
| Steam to Carbon Ration | 0.36 | 0.34 | 0.28 | 0.27 | 0.26 | 0.27 | 0.27 | 0.29 | 0.33 |
| Activation Purge Gas: | | | | | | | | | |
| Nitrogen, SCFH | | | | 0.54 | 0.63 | 0.71 | 0.57 | 0.58 | 6.4 |
| Breathing Air, SCFH | | | | 2900 | 2900 | 2900 | 2900 | 2900 | |
| Hydrogen, SCFH | | | | 0.41 | 0.41 | 0.39 | 0.44 | 0.45 | |
| Activation Period, Hrs. | | | | | | | | | 1.0 |

(1)Pipe diameters/180° of twist in nickel strip (⅛" thick).
(4)Activation
(5)Cu. ft. of methane produced per hr./cu. ft. of catalyst.
(6)Cu. ft. of methane produced per hr./sq. ft. of catalyst.

TABLE 2

METHANATION USING TURBULATOR-TYPE CATALYST
SELECTIVE CONVERSION TO METHANE

| RUN NO | SAMPLE NO | CF CO In Feed | CF Product | % CH$_4$ In Product | CF CH$_4$ In Product | % Conversion CH$_4$/CO × 100 |
|---|---|---|---|---|---|---|
| 12 | 18 | 7 | 28.7 | 24.8 | .12 | 101.7 |
| 13 | 19 | 12.9 | 24.3 | 47.3 | 11.5 | 89.1 |
| 13 | 20 | 13.4 | 24.5 | 42.8 | 10.5 | 78.3 |
| 13 | 21 | 13.4 | 26.9 | 37.8 | 10.2 | 75.9 |
| 13 | 22 | 13.4 | 26.2 | 37.9 | 9.9 | 74.1 |
| 14 | 23 | 11.7 | 20.8 | 54.5 | 11.3 | 96.9 |
| 14 | 24 | 12.0 | 18.3 | 49.4 | .0 | 75.3 |
| 14 | 25 | 13.2 | 21.6 | 54.0 | 11.7 | 88.4 |
| 14 | 26 | 14.1 | 23.4 | 51.0 | 11.9 | 84.6 |
| 14 | 27 | 14.1 | 24.0 | 51.2 | 12.3 | 87.1 |
| 14 | 28 | 14.1 | 23.6 | 55.1 | 13.0 | 92.2 |
| 14 | 29 | 14.1 | 24.0 | 52.1 | 12.5 | 88.7 |
| 14 | 30 | 14.1 | 22.5 | 52.1 | 11.7 | 83.1 |

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. In a process for producing methane by reacting carbon monoxide with hydrogen, the improvement comprising feeding a gas containing hydrogen and carbon monoxide into at least one reaction tube containing an annular, spiral-shaped passageway defined by a helical, nickel-containing catalyst which is wrapped around a central cooling duct; said spiral-shaped passageway having a Y factor of 3.0 or less, said Y factor being defined by the equation $Y = L/D$ wherein L is the length of a single twist and D is the diameter of the reaction tube; passing a cooling medium through said cooling duct and cooling the exterior of said reaction tube to remove the heat of reaction.

2. The method of claim 1, wherein said spiral catalyst is a ribbon wrapped on edge about the central cooling duct.

3. The method of claim 1, wherein said tubular reactor is in the form of an outer sheath closed at one end and containing the catalyst and cooling duct, the cooling duct terminating short of the closed end of the sheath and wherein said feed gas is passed through said central duct for cooling, reversing its flow at said terminal end for flow through said spiral passageway in contact with said helical catalyst.

4. The process of claim 1 wherein said catalyst has a Y factor of 2 to 3.

* * * * *